United States Patent
Nagae et al.

(10) Patent No.: US 10,307,125 B2
(45) Date of Patent: Jun. 4, 2019

(54) IMAGE PROCESSING APPARATUS, X-RAY DIAGNOSTIC APPARATUS, AND IMAGE PROCESSING METHOD

(71) Applicant: TOSHIBA MEDICAL SYSTEMS CORPORATION, Otawara-Shi (JP)

(72) Inventors: Ryoichi Nagae, Nasushiobara (JP); Yasuto Hayatsu, Otawara (JP); Yoshiaki Iijima, Nasushiobara (JP); Naoki Uchida, Utsunomiya (JP); Yuichiro Watanabe, Yaita (JP); Takuya Sakaguchi, Utsunomiya (JP)

(73) Assignee: Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 15/130,483

(22) Filed: Apr. 15, 2016

(65) Prior Publication Data

US 2016/0350913 A1 Dec. 1, 2016

(30) Foreign Application Priority Data

Jun. 1, 2015 (JP) .................................. 2015-111546

(51) Int. Cl.
G06K 9/00 (2006.01)
A61B 6/00 (2006.01)
(Continued)

(52) U.S. Cl.
CPC ................ *A61B 6/487* (2013.01); *A61B 6/12* (2013.01); *A61B 6/504* (2013.01); *A61B 6/5217* (2013.01);
(Continued)

(58) Field of Classification Search
CPC .................... A61B 6/504; A61B 6/487; G06T 2207/30104; G06T 2207/10116;
(Continued)

(56) References Cited

U.S. PATENT DOCUMENTS 7,930,014 B2 * 4/2011 Huennekens .......... A61B 6/504
382/159
9,833,212 B2 * 12/2017 Nagae .................. A61B 6/5211
(Continued)

FOREIGN PATENT DOCUMENTS

CN 100399996 C 7/2008
JP 2003-190148 A 7/2003
(Continued)

OTHER PUBLICATIONS

Combined Office Action and Search Report dated Jul. 19, 2017 in Chinese Patent Application No. 201610380035.1 (with English translation of categories of cited documents).

(Continued)

*Primary Examiner* — Bhavesh M Mehta
*Assistant Examiner* — Ian L Lemieux
(74) *Attorney, Agent, or Firm* — Oblon, McClelland, Maier & Neustadt, L.L.P.

(57) ABSTRACT

According to one embodiment, an image processing apparatus includes processing circuitry. The processing circuitry obtains a parameter value representing temporal information on blood flow for each pixel of multiple image data items, and generates a parameter image by determining a pixel value of each pixel according to the parameter value representing the temporal information on blood flow. The processing circuitry further generates a composite image of an X-ray fluoroscopic image of an object obtained in real time and a road map image using at least a part of the parameter image, and causes a display to display the composite image.

17 Claims, 15 Drawing Sheets

(51) Int. Cl.
  *A61B 6/12* (2006.01)
  *G06T 7/11* (2017.01)
  *G06T 7/174* (2017.01)
  *A61B 6/06* (2006.01)

(52) U.S. Cl.
  CPC .............. G06T 7/11 (2017.01); G06T 7/174 (2017.01); *A61B 6/06* (2013.01); *A61B 6/4441* (2013.01); *G06T 2207/10121* (2013.01); *G06T 2207/30101* (2013.01); *G06T 2207/30104* (2013.01)

(58) Field of Classification Search
  CPC . G06T 2207/10121; G06T 2207/30101; G06T 7/11; G06T 7/174; G06T 7/187; G06T 7/20
  See application file for complete search history.

(56) References Cited

U.S. PATENT DOCUMENTS

| | | | | |
|---|---|---|---|---|
| 2002/0151781 A1* | 10/2002 | Ohishi | ............ | A61B 6/466 600/407 |
| 2006/0184006 A1* | 8/2006 | Chen | ............ | A61B 6/12 600/416 |
| 2009/0016587 A1* | 1/2009 | Strobel | ............ | A61B 6/469 382/130 |
| 2009/0110252 A1* | 4/2009 | Baumgart | ............ | A61B 6/481 382/130 |
| 2010/0135562 A1* | 6/2010 | Greenberg | ............ | G06F 19/321 382/131 |
| 2010/0329523 A1 | 12/2010 | Ostermeier et al. | | |
| 2011/0075904 A1* | 3/2011 | Yoshikawa | ............ | A61B 8/06 382/131 |
| 2011/0182492 A1* | 7/2011 | Grass | ............ | A61B 6/4441 382/131 |
| 2013/0077839 A1* | 3/2013 | Horz | ............ | A61B 6/481 382/130 |
| 2015/0150526 A1* | 6/2015 | Ohishi | ............ | A61B 6/463 378/62 |
| 2015/0179148 A1* | 6/2015 | Auvray | ............ | A61B 6/12 345/629 |
| 2015/0201897 A1* | 7/2015 | Kyriakou | ............ | A61B 5/489 600/419 |
| 2015/0265228 A1* | 9/2015 | Kyriakou | ............ | A61B 5/0075 600/340 |
| 2016/0035103 A1 | 2/2016 | Stawiaski et al. | | |
| 2016/0078621 A1* | 3/2016 | Nagae | ............ | G06T 7/0016 382/130 |
| 2016/0143605 A1* | 5/2016 | Nagae | ............ | A61B 6/5211 378/62 |

FOREIGN PATENT DOCUMENTS

| | | |
|---|---|---|
| JP | 2004-321390 A | 11/2004 |
| JP | 2008-264274 | 11/2008 |
| WO | WO 2014/162273 A1 | 10/2014 |

OTHER PUBLICATIONS

Combined Office Action and Search Report dated Mar. 12, 2018 in Chinese Patent Application No. 201610380035.1 with English translation of categories of cited documents, 9 pages.
Office Action dated Apr. 2, 2019, in corresponding Japanese Patent Application No. 2015-111546, citing documents AO and AP therein.

\* cited by examiner

IMAGE PROCESSING APPARATUS, X-RAY DIAGNOSTIC APPARATUS, AND IMAGE PROCESSING METHOD

CROSS-REFERENCE TO RELATED APPLICATIONS

This application claims the benefit of priority of Japanese Patent Application No. 2015-111546, filed Jun. 1, 2015, the entire contents of which are incorporated herein by reference.

FIELD

Embodiments described herein relate generally to an image processing apparatus, an X-ray diagnostic apparatus, and an image processing method.

BACKGROUND

In some cases of catheter therapy, a user causes an X-ray fluoroscopic image based on X-ray imaging by an X-ray diagnostic apparatus to be displayed in real time, and performs a procedure while recognizing the position of a catheter in the X-ray fluoroscopic image.

Techniques for assisting the procedure of a user for catheter therapy include a technique that displays a real-time X-ray fluoroscopic image overlaid with an image of blood vessels stained with a contrast medium, a white blank image of this image, a three-dimensional vascular image or the like as a catheter road map image. This type of techniques allow the position of a catheter appearing in a real-time X-ray fluoroscopic image, and a road map image displaying the flowing direction of bloodstream at the same site to be recognized at the same time. This facilitates the user's grasping the catheter advancing direction even when the site has a complicated structure, and allows a correct catheter operation.

Unfortunately, in the case of using an image of blood vessels stained with a contrast medium or a white blank image of this image as a road map image, it is difficult to discriminate whether a portion where a blood vessel appears branched is actual branching of the identical blood vessel or an intersection between different blood vessels located at the front and rear in the depth direction of the image. On the other hand, in the case of using a three-dimensional vascular image as a road map image, it is easy to discriminate between branching of the identical blood vessel and an intersection of blood vessels, but great efforts and time are required to prepare the three-dimensional vascular image as the road map image, in the first place. Alignment between a prepared three-dimensional vascular image and a real-time X-ray fluoroscopic image is significantly difficult. The images often deviate from each other. The positional deviation makes the procedure of the user difficult.

The present invention has an object to provide an image processing apparatus, an X-ray diagnostic apparatus, and an image processing method capable of displaying an image facilitating discrimination between branching of the identical blood vessel and an intersection of blood vessels.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an image processing apparatus, an X-ray diagnostic apparatus, and an image processing method according to embodiments of the present invention with reference to the drawings.

In general, according to one embodiment, an image processing apparatus includes processing circuitry. The processing circuitry obtains a parameter value representing temporal information on blood flow for each pixel of multiple image data items, and generates a parameter image by determining a pixel value of each pixel according to the parameter value representing the temporal information on blood flow. The processing circuitry further generates a composite image of an X-ray fluoroscopic image of an object obtained in real time and a road map image using at least a part of the parameter image, and causes a display to display the composite image.

Figure 1:
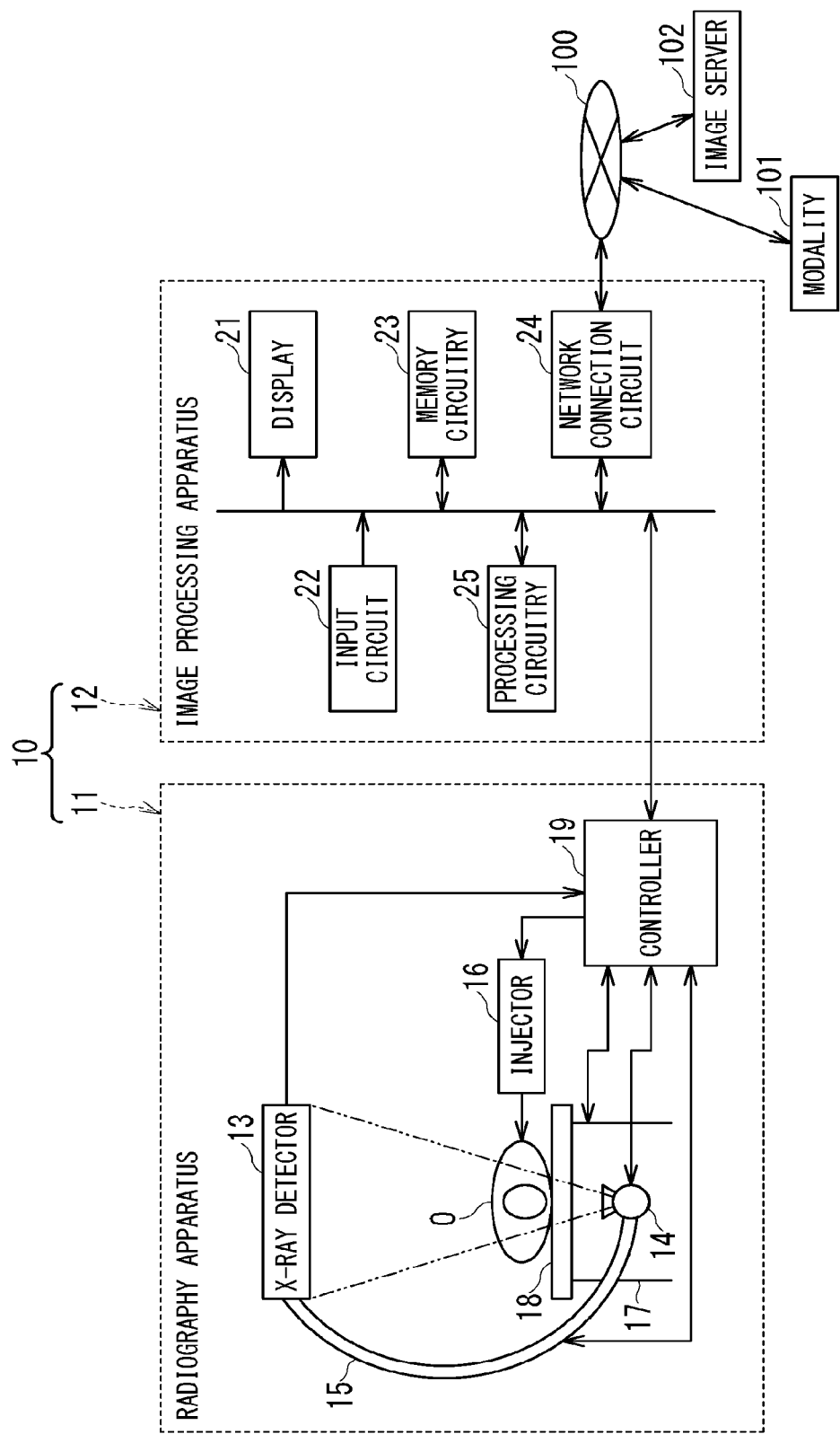
FIG. 1 is a block diagram showing an example of an X-ray diagnostic apparatus according to one embodiment of the present invention.

FIG. 1 is a block diagram showing an example of an X-ray diagnostic apparatus 10 according to one embodiment of the present invention.

As shown in FIG. 1, the X-ray diagnostic apparatus 10 includes an X-ray radiography apparatus 11, and an image processing apparatus 12. The radiography apparatus 11 of the X-ray diagnostic apparatus 10 is typically installed in a laboratory, and configured so as to generate image data on an object O. The image processing apparatus 12 is installed in an operation room adjacent to the laboratory, and configured so as to generate and display an image based on the image data. The image processing apparatus 12 may be installed in the laboratory where the radiography apparatus 11 is installed.

The radiography apparatus 11 includes an X-ray detector 13, an X-ray source 14, a C-arm 15, an injector 16, a bed 17, a tabletop 18, and a controller 19.

The X-ray detector 13 is provided at an end of the C-arm 15 so as to disposed opposite to the X-ray source 14 sandwiching the object O supported by the tabletop (catheter table) 18 of the bed 17. The X-ray detector 13 is made up of a flat panel detector (FPD), detects X-rays with which the X-ray detector 13 has been irradiated, and outputs projection data on the basis of the detected X-rays. The projection data is provided for the image processing apparatus 12 via the controller 19. The X-ray detector 13 may include an image intensifier, and a TV camera.

The X-ray source 14 is provided at the other end of the C-arm 15, and includes an X-ray tube and an X-ray collimator. The X-ray collimator is a collimator to restrict an X-ray irradiation range, and includes multiple lead blades for example. The X-ray collimator is controlled by the controller 19 to adjust the range irradiated with X-rays from the X-ray tube.

The C-arm 15 holds the X-ray detector 13 and the X-ray source 14 in an integrated manner. The C-arm 15 is driven under control by the controller 19, thereby allowing the X-ray detector 13 and the X-ray source 14 to move around the object O in an integrated manner.

The radiography apparatus 11 of the X-ray diagnostic apparatus 10 may be of a biplane type, which has two X-ray irradiation systems each including an X-ray detector 13, an X-ray source 14 and a C-arm 15. In the case of including the biplane type radiography apparatus 11, the X-ray diagnostic apparatus 10 can emit X-rays in two directions from a floor-standing C-arm and a ceiling traveling Ω arm in a separated manner, and obtain a biplane image (a frontal image and a lateral image). Alternatively, instead of the ceiling traveling Ω arm, a ceiling traveling C arm or the like may be used.

The injector 16 is a device that is controlled by the controller 19, and injects a contrast medium through a catheter (catheter tube) inserted to a predetermined site (affected area) of the object O. The timing of injecting the contrast medium and stopping the injection, and the intensity and injection speed of the contrast medium are automatically controlled by the controller 19. The injector 16 may be prepared as an external isolated device different from the X-ray diagnostic apparatus 10. In this case, the X-ray diagnostic apparatus 10 does not include the injector 16. In every case irrespective whether the injector 16 is prepared at the outside or not, the injector 16 is not necessarily controlled by the controller 19. For example, the injector 16 may accept an instruction from the user through an input device provided at the injector 16, and inject the contrast medium at the intensity, speed and timing according to this instruction.

The bed 17 is installed on the floor, and supports the tabletop 18. The bed 17 is controlled by the controller 19 to move the tabletop 18 in the horizontal direction and the vertical direction and roll this table.

The controller 19 controls the X-ray detector 13 and the injector 16 under control by the image processing apparatus 12 to execute X-ray fluoroscopic imaging of the object O and create projection data, and provide the data for the image processing apparatus 12. For example, the controller 19 is controlled by the image processing apparatus 12 to generate projection data items before and after administration of the contrast medium, and provide the data items for the image processing apparatus 12.

In the case where the X-ray diagnostic apparatus 10 has a configuration capable of rotational DSA (Digital Subtraction Angiography) imaging, the controller 19 is controlled by the image processing apparatus 12 to execute rotational DSA imaging, generate projection data items before and after administration of the contrast medium, and provide the data for the image processing apparatus 12. The rotational DSA imaging generates image data (mask image data) before contrast medium injection and image data (contrast image data) after contrast medium injection on the identical site of the object O. In the case where rotational DSA imaging is possible, the X-ray diagnostic apparatus 10 can obtain a three-dimensional vascular image (3D vascular image) on the basis of the contrast image data and the mask image obtained by rotational DSA imaging.

The controller 19 includes at least a processor and memory circuitry. The controller 19 is controlled by the image processing apparatus 12 according to a program stored in the memory circuitry to control the X-ray irradiation system to thereby execute X-ray fluoroscopic imaging of the object O and create image data, and provide the data for the image processing apparatus 12.

Although the example of the case where the controller 19 and the image processing apparatus 12 are connected to each other by wire is shown in FIG. 1, the controller 19 and the image processing apparatus 12 may be connected to each other and send/receive data between them via a network 100.

The memory circuitry of the controller 19 provides a work area that temporarily stores programs executed by the processor of the controller 19, and data. Furthermore, the memory circuitry of the controller 19 stores a boot-up program for the radiography apparatus 11, a control program for the radiography apparatus 11, and various types of data required to execute these programs. The memory circuitry of the controller 19 has a configuration that includes a processor-readable recording medium, such as a magnetic or optical recording medium or a semiconductor memory. Some or all of the programs and data in the memory circuitry may be configured to be downloaded via an electronic network.

As shown in FIG. 1, the image processing apparatus 12 includes a display 21, an input circuit 22, memory circuitry 23, a network connection circuit 24, and processing circuitry 25.

The display 21 may be, for example, a general display output device, such as a liquid crystal display or an OLED (Organic Light Emitting Diode) display, and displays, for example, a composite image of a road map image generated by the processing circuitry 25 and a fluoroscopic image, according to control by the processing circuitry 25.

The input circuit 22 may be, for example, a general input device, such as a track ball, a switch button, a mouse, a keyboard, or a ten key pad, and outputs an operational input signal according to an operation by the user to the processing circuitry 25.

The memory circuitry 23 has a configuration including a processor-readable memory medium, such as a magnetic or optical memory medium or a semiconductor memory. Alternatively, some or all of programs and data in the recording medium may be configured to be downloaded by communication via an electronic network. The memory circuitry 23 is controlled by the processing circuitry 25 to store, for example, image data output from the radiography apparatus 11.

The network connection circuit 24 is implemented with various protocols for information communication according to the mode of the network 100. The network connection circuit 24 connects the X-ray diagnostic apparatus 10 and another apparatus, such as a modality 101, to each other according to the various protocols. Here, the network 100 means any of general information communication networks that use telecommunication techniques, and includes not only wireless and wired LANs (Local Area Networks), such as hospital main LANs and the Internet, but also a telephone communication network, an optical fiber communication network, a cable communication network, a satellite communication network, and the like.

The image processing apparatus 12 may receive image data from the modality 101 or an image server 102 connected via the network 100. In this case, medical image data output from the modality 101 or reconstructed image data is received via the network 100 and stored in the memory circuitry 23. The modality 101 is, for example, a medical image diagnostic apparatus, such as an X-ray CT (Computed Tomography) apparatus, an MRI (Magnetic Resonance Imaging) apparatus, an ultrasonic diagnostic apparatus, or an X-ray diagnostic apparatus, and may be an apparatus that can generate medical image data on the basis of projection data obtained by imaging on an object (patient). The image server 102 is, for example, a server for long-term storage of images that is included in a PACS (Picture Archiving and Communication System), and stores the medical image data generated by the modality 101 connected via the network 100 or the reconstructed image data.

The processing circuitry 25 is a processor that executes a process of displaying an image facilitating discrimination between branching of the identical blood vessel and an intersection of blood vessels by reading the program stored in the memory circuitry 23 and executing the program.

Figure 2:
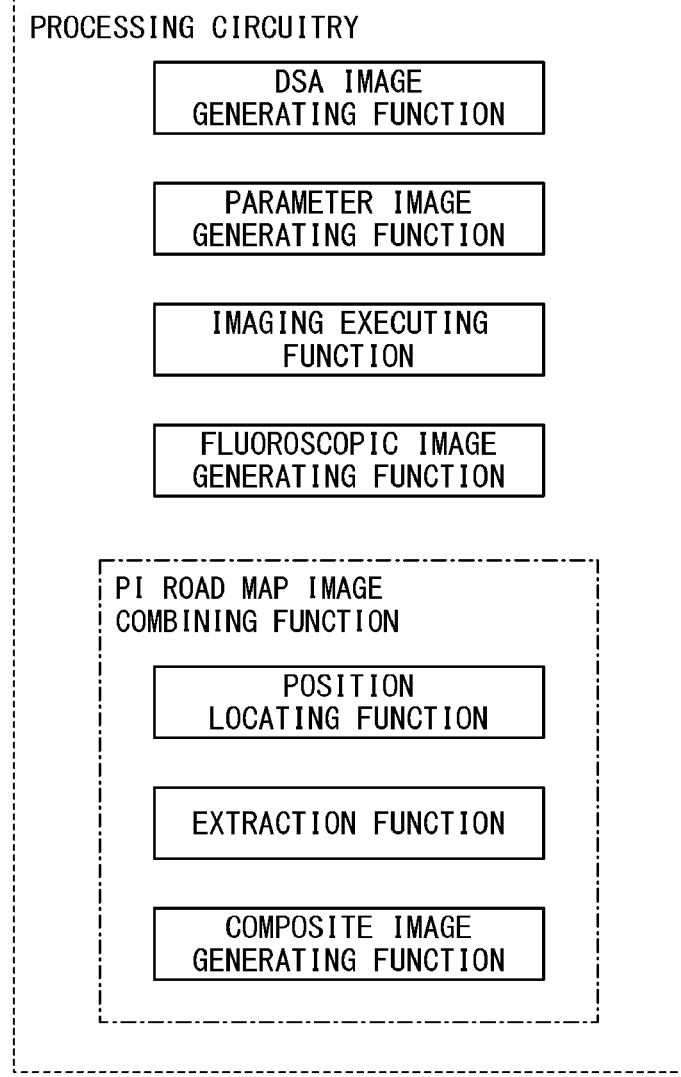
FIG. 2 is a block diagram showing an example of functions achieved by the processing circuitry.

FIG. 2 is a block diagram showing an example of functions achieved by the processing circuitry 25.

The processing circuitry 25 achieves at least a DSA image generating function, a parameter image generating function, an imaging executing function, a fluoroscopic image generating function, and a PI road map image combining function. The PI road map image combining function includes at least a position locating function, an extraction function, and a composite image generating function. These functions are stored in the memory circuitry 23 in forms of programs.

The DSA image generating function is a function that controls the imaging executing function, and controls the radiography apparatus 11 via the controller 19, thereby generating temporally consecutive DSA images of the object O.

The parameter image generating function is a function that obtains parameter values representing temporal information on blood flow on the pixel-by-pixel basis, based on the time-intensity curve on each pixel in image data items, such as image data items on multiple DA (Digital Angiography) images of the object O (e.g., contrast images) that are temporally consecutive, or image data items on multiple DSA images, and determines the pixel value of each pixel according to the parameter values representing the temporal information on blood flow, thereby generating a parameter image using the parameter values representing the temporal information on blood flow. The following description is made on an example where the parameter image generating function obtains the parameter values representing temporal information on blood flow on the pixel-by-pixel basis, based on the time-intensity curve on each pixel in temporally consecutive DSA images of the object O and determines the pixel value of each pixel according to the parameter values representing the temporal information on blood flow to thereby generate the parameter image using the parameter values representing the temporal information on blood flow.

The imaging executing function is a function that controls the radiography apparatus 11 through the controller 19 to causes the radiography apparatus 11 to perform X-ray fluoroscopic imaging of the object O.

The fluoroscopic image generating function is a function that generates fluoroscopic images in real time on the basis of projection data obtained by X-ray fluoroscopic imaging of the object O, allows the image to be subjected to the PI road map image combining function, and causes the display 21 to display the image.

The PI road map image combining function is a function that generates the road map image using the parameter values representing the temporal information on blood flow, generates the composite image of the fluoroscopic image of the object O obtained in real time and the road map image, and causes the display 21 to display the image. In the following description, the road map image generated using the parameter values representing the temporal information on blood flow is sometimes referred to as a PI road map image.

The PI road map image combining function may use a fluoroscopic image having been subjected only to gradation conversion when using the X-ray fluoroscopic image generated in real time by the fluoroscopic image generating function for the composite image. An image from which a pervious X-ray fluoroscopic image is subtracted to extract a device, or an image where both the images are added to each other at a predetermined ratio (hereinafter, both the images are collectively referred to as fluoroscopic images) may be used. Here, the device is a therapeutic device inserted into the object O, for example, a catheter or a guidewire. In this embodiment, the fluoroscopic image and the processed fluoroscopic image are collectively referred to as fluoroscopic images in some cases.

The position locating function of the PI road map image combining function is a function that locates, in the parameter image, the position of a portion of interest (e.g., the distal end of a catheter, a marker provided at the catheter, etc.) of the therapeutic device (e.g., catheter) inserted to a site of the object O. The position locating function of the PI road map image combining function is a function that obtains information on an insertion target position (e.g., the position of a therapy target portion etc.) of the device. The information on the target position of the device may be input by a user through the input circuit 22, or preliminarily stored in the memory circuitry 23. In the following description, an example is provided where the distal end position of the catheter is used as the portion of interest of the device.

The extraction function of the PI road map image combining function is a function that extracts pixels having parameter values in a predetermined range including the parameter value at the position of the portion of interest of the device.

Furthermore, the extraction function has a function that extracts pixels having parameter values ranging from the parameter value at the position of the portion of interest of the device to the parameter at the target position of the device. In this case, it is preferred that the extraction function have a function that sequentially scan pixels from the pixel corresponding to the position of the portion of interest of the device in the direction approaching the parameter value at the target position of the device, and extract the pixels scanned until reaching the target position of the device.

The extraction function further has a function that extracts the pixels in a predetermined region including the position of the portion of interest of the device, and a function that extracts the pixels in a predetermined region including the target position of the device.

The composite image generating function of the PI road map image combining function is a function that generates the PI road map image using at least a part of the parameter image. More specifically, this function generates, as the PI road map image, the parameter image itself or a partial image corresponding to the pixels extracted by the extraction function in the parameter image. The composite image generating function has a function that generates a composite image of the fluoroscopic image of the object O obtained in real time and the road map image, and causes the display 21 to display the image.

Next, an example of the operation of the X-ray diagnostic apparatus 10 that includes the image processing apparatus 12 according to this embodiment is described.

Figure 3:
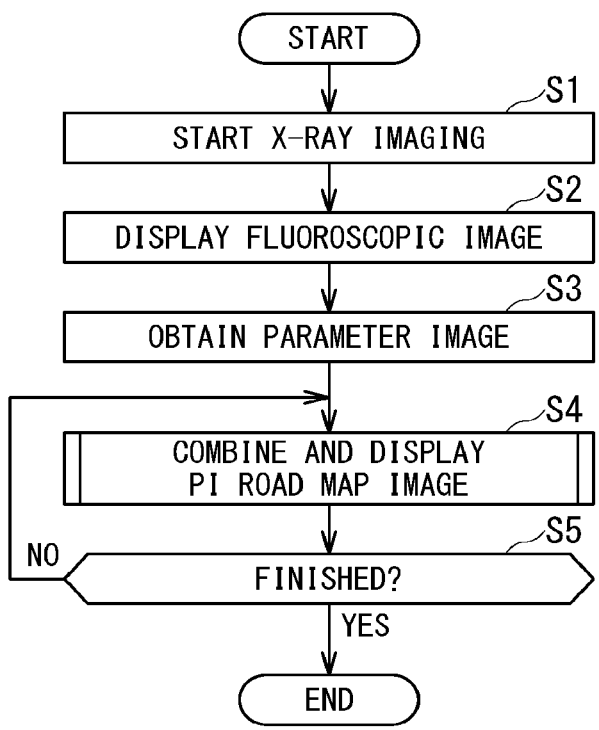
FIG. 3 is a flowchart showing an example of procedures for displaying an image facilitating discrimination between branching of the identical blood vessel and an intersection of blood vessels by the processing circuitry shown in FIG. 1.

FIG. 3 is a flowchart showing an example of procedures for displaying an image facilitating discrimination between branching of the identical blood vessel and an intersection of blood vessels by the processing circuitry 25 shown in FIG. 1. In FIG. 3, symbols S assigned numerals represent the respective steps of the flowchart.

First, in step S1, the processing circuitry 25 uses the imaging executing function to control the radiography apparatus 11 through the controller 19, thereby achieving X-ray fluoroscopic imaging of the object O while administering a contrast medium.

Next, in step S2, the processing circuitry 25 uses the fluoroscopic image generating function to generate fluoroscopic images in real time on the basis of projection data obtained by X-ray fluoroscopic imaging of the object O, allow the image to be subjected to the PI road map image combining function, and cause the display 21 to display the images.

Next, in step S3, the processing circuitry 25 uses the PI road map image combining function to obtain, from the memory circuitry 23, the parameter image where the pixel values of pixels are determined according to the parameter values representing the temporal information on blood flow.

Next, in step S4, the processing circuitry 25 uses the PI road map image combining function to generate the road map image (the road map image using at least a part of the parameter image) using the parameter values representing the temporal information on blood flow, generates the composite image of the fluoroscopic image of the object O obtained in real time and the PI road map image, and causes the display 21 to display the image.

Next, in step S5, the processing circuitry 25 uses the PI road map image combining function to determine whether to finish displaying the composite image or not. When a finish instruction by the user is received through the input circuit 22 or another image is to be displayed, the series of procedures is finished. On the contrary, when the series of procedures is not to be finished, the processing returns to step S4.

The above procedures can achieve displaying an image facilitating discrimination between branching of the identical blood vessel and an intersection of blood vessels.

Here, the parameter image using the parameter values representing the temporal information on blood flow according to this embodiment is described.

Figure 4:
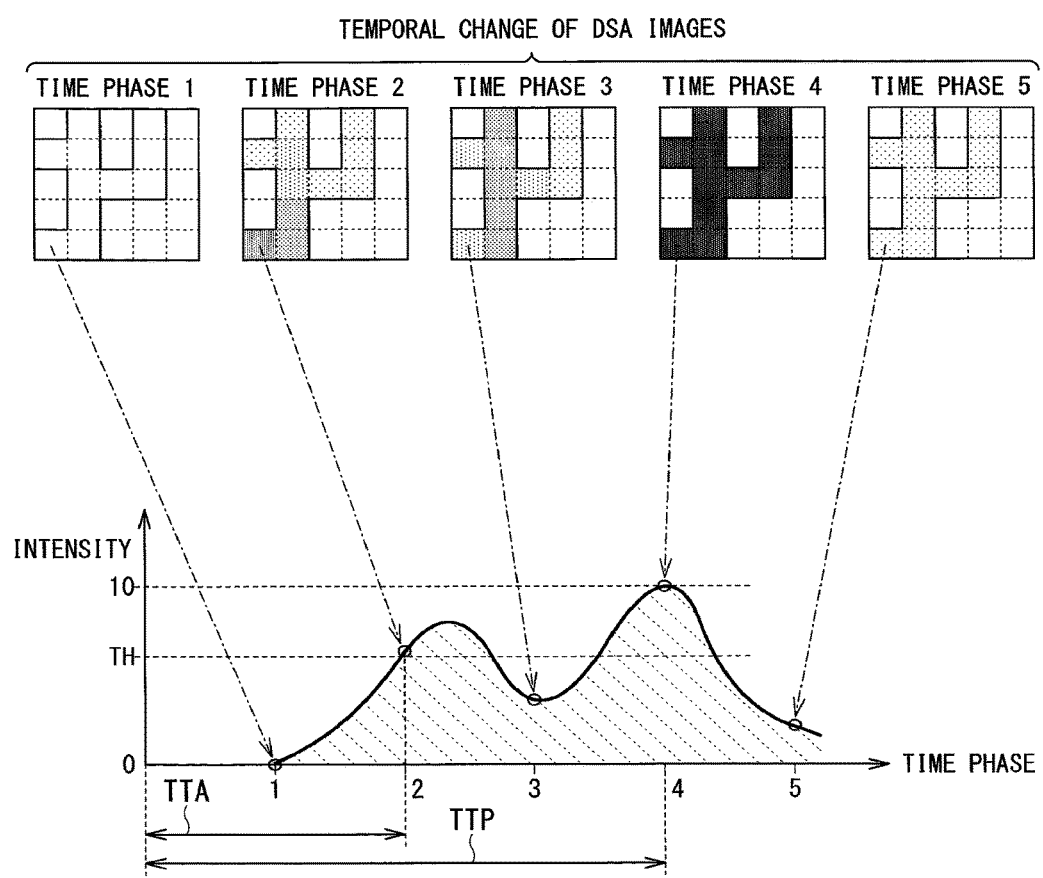
FIG. 4 is a diagram for illustrating the parameter image where the pixel values of pixels are determined according to the parameter values representing the temporal information on blood flow.

FIG. 4 is a diagram for illustrating the parameter image where the pixel values of pixels are determined according to the parameter values representing the temporal information on blood flow.

The parametric imaging is, for example, a process of imaging a single or multiple parameters in color or grayscale. The parametric imaging includes a fluoroscopic image generated by the fluoroscopic image generating function, in a broad sense. This is because the pixel value of each pixel of the fluoroscopic image represents the value of X-ray transmittance as a parameter.

In a narrow sense, the parametric imaging is a process that calculates the parameter value other than the X-ray transmittance on a pixel-by-pixel basis on the basis of the fluoroscopic image, and performs imaging in color or grayscale on the basis of a color map or a grayscale map. In this embodiment, the parametric imaging in a narrow sense is described. In the following description, an image generated by parametric imaging in a narrow sense is referred to as a parameter image.

The upper part of FIG. 4 shows DSA images in respective time phases. The lower part of FIG. 4 shows an example of a curve (time-intensity curve) representing temporal change in contrast medium intensity, focused on one pixel.

For example, the case is considered where according to imaging in an identical imaging region of the identical object O by the X-ray diagnostic apparatus 10, six projection data items on X-ray images are generated by the DSA image generating function sequentially at time t=0 before administration of the contrast medium, and then time t=1, 2, 3, 4 and 5 after administration of the contrast medium. In this case, by subtracting the X-ray image at t=0 (mask image) from each X-ray image after administration of the contrast medium, image data on five frames of DSA images (difference images) corresponding to t=1, 2, 3, 4 and 5, respectively, are obtained (see the upper part of FIG. 4).

In the upper part of FIG. 4, t=1 is defined as time phase 1, and t=2 is defined as time phase 2 (and so forth). For example, in a region where multiple blood vessels intersect with each other, multiple local maximum values of the contrast medium intensity may sometimes be observed as shown in the lower part of FIG. 4 even with only one time of injection of the contrast medium.

Here, the processing circuitry 25 uses the parameter image generating function to calculate change in time phase (t=1 to 5) of the pixel values on a pixel-by-pixel basis through the five frames of DSA images, thereby calculating the time-intensity curve on each pixel. The lower part of FIG. 4 is an example of the contrast medium time-intensity curve focused on one pixel at the lower left of each DSA image (5×5 pixels in this example). The ordinate axis represents the intensity of contrast medium. The abscissa axis represents the time phase (elapsed time t).

More specifically, as the contrast medium has a higher X-ray absorptance than body tissue has, the amount of dose at the X-ray detection element corresponding to the position with high contrast medium intensity is low. Consequently, the contrast medium is projected darker than the surroundings in the X-ray image. Each pixel value of the DSA image is the difference from the pixel value at the same position in the mask image (before administration of the contrast medium). Consequently, if one pixel at the same position is focused and an appropriate process such as sign inversion is applied to the change in time phase of the pixel value of the pixel, the change becomes equivalent to the temporal change in contrast medium intensity.

In this embodiment, the parameters used for the parameter image are parameters representing temporal information on blood flow. The parameters representing temporal information on blood flow include, for example, TTP (Time To Peak) and TTA (Time To Arrival) which are shown in the lower part of FIG. 4.

TTP is a parameter having, as a parameter value, a time phase where the contrast medium intensity reaches a peak (maximum intensity arrival time). TTA is a parameter having, as a parameter value, a time phase where the contrast medium intensity exceeds a threshold TH at the first time (e.g., time in which the contrast medium reaches each pixel) on the temporal change curve of contrast medium intensity.

Subsequently, procedures are described for generating a composite image by combining the PI road map image generated using at least a part of the parameter image using the parameter value representing temporal information on blood flow with the fluoroscopic image of the object O obtained in real time.

Figure 5:
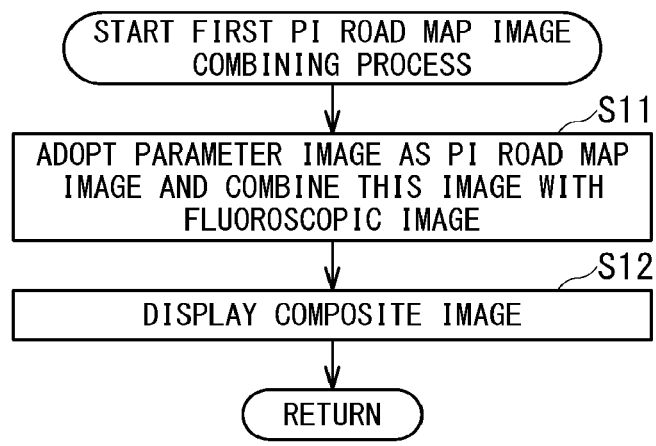
FIG. 5 is a subroutine flowchart showing an example of a first procedure of a PI road map image combining process executed by the PI road map image combining function in step S4 of FIG. 3.

FIG. 5 is a subroutine flowchart showing an example of a first procedure of a PI road map image combining process executed by the PI road map image combining function in step S4 of FIG. 3.

Figure 6:
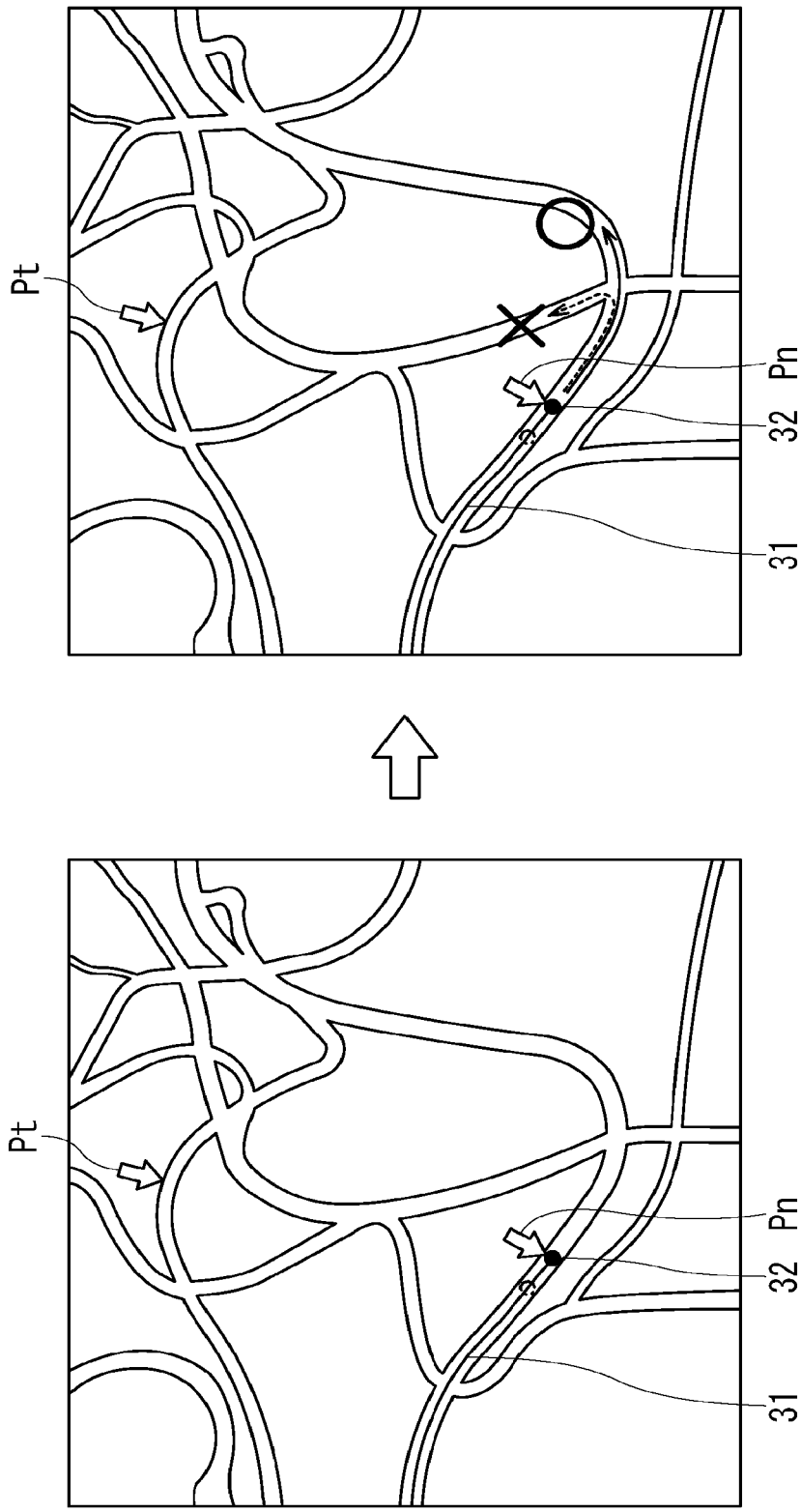
FIG. 6 is a diagram illustrating an example of a conventional road map image where a white blank image of an image with blood vessels stained with the contrast medium is used as the road map image.
Figure 7:
FIG. 7 is a diagram illustrating an example of a composite image using a PI road map image generated by a first PI road map image combining process shown in FIG. 5.

FIG. 6 is a diagram illustrating an example of a conventional road map image (hereinafter, referred to as a fluoroscopic road map image) where a white blank image of an image with blood vessels stained with the contrast medium is used as the road map image. FIG. 7 is a diagram illustrating an example of a composite image using a PI road map image generated by a first PI road map image combining process shown in FIG. 5.

A case is now considered where the user intends to insert the catheter 31 as the therapeutic device into a blood vessel, and move the distal end 32 of the catheter from the current position Pn to the target position Pt as a therapy target.

As shown in FIGS. 6 and 7, the fluoroscopic image includes an image of a distal end 32 of a catheter 31. Here, as shown in FIG. 6, according to the composite image using the conventional fluoroscopic road map image, it is difficult to discriminate between branching of the identical blood vessel and the intersection of blood vessels (see right part of FIG. 6).

Thus, the image processing apparatus 12 according to this embodiment generates the PI road map image using at least a part of the parameter image using the parameter value representing temporal information on blood flow, and combines this image with the fluoroscopic image of the object O obtained in real time to generate the composite image.

The first PI road map image combining process shown in FIG. 5 is a process of adopting the entire parameter image as the PI road map image.

First, in step S11, the processing circuitry 25 uses the composite image generating function of the PI road map image combining function to generate, as the PI road map image, the entire parameter image using the parameter value representing temporal information on blood flow, and combines this image with the fluoroscopic image of the object O obtained in real time to generate the composite image.

Next, in step S12, the processing circuitry 25 causes the display 21 to display the composite image generated by the composite image generating function of the PI road map image combining function (see FIG. 7), and advances the processing to step S5 in FIG. 3.

The above procedures can adopt the entire parameter image as the PI road map image. As shown in FIG. 7, the vascular image shown in the PI road map image generated by the first PI road map image combining process has pixel values according to the parameter values representing temporal information on blood flow. Consequently, the PI road map image allows the user to easily discriminate between branching of the identical blood vessel and the intersection of blood vessels.

Alternatively, in step S11, the processing circuitry 25 may use the processed fluoroscopic image generating process of the PI road map image combining function to generate a mask image from one of the fluoroscopic images, generate a processed fluoroscopic image by a process of subtracting the mask image from the fluoroscopic image generated in real time, and use the processed fluoroscopic image as the fluoroscopic image. It should be noted that the mask image in this processed fluoroscopic image generating process is according to a concept different from that of the mask image that is used for the DSA image generation and is before injection of the contrast medium.

Figure 8:
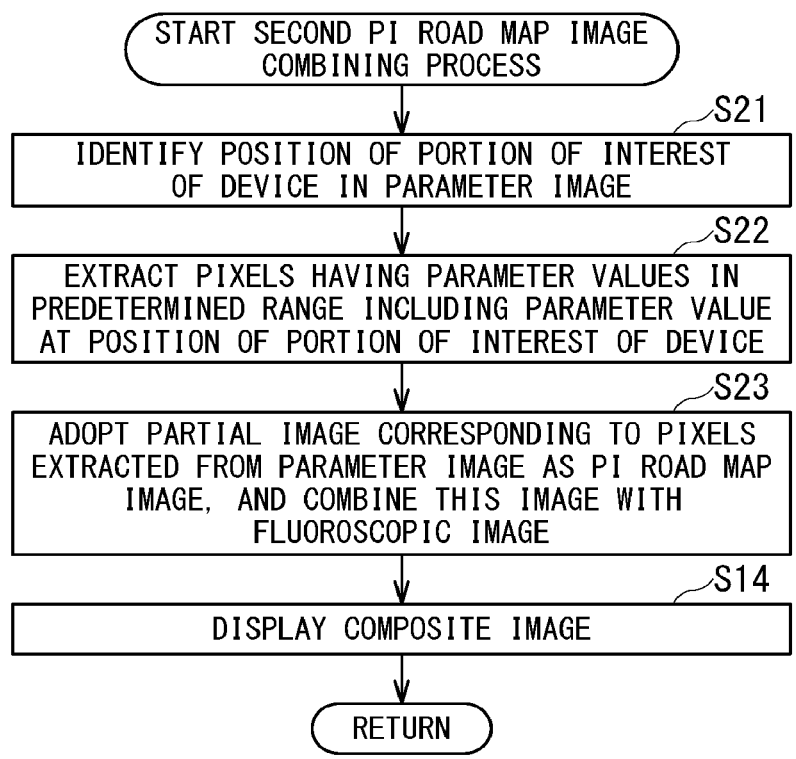
FIG. 8 is a subroutine flowchart showing an example of a second procedure of a PI road map image combining process executed by the PI road map image combining function in step S4 of FIG. 3.

FIG. 8 is a subroutine flowchart showing an example of a second procedure of a PI road map image combining process executed by the PI road map image combining function in step S4 of FIG. 3. Steps equivalent to those in FIG. 5 are assigned the same symbols, and redundant description is omitted.

Figure 9:
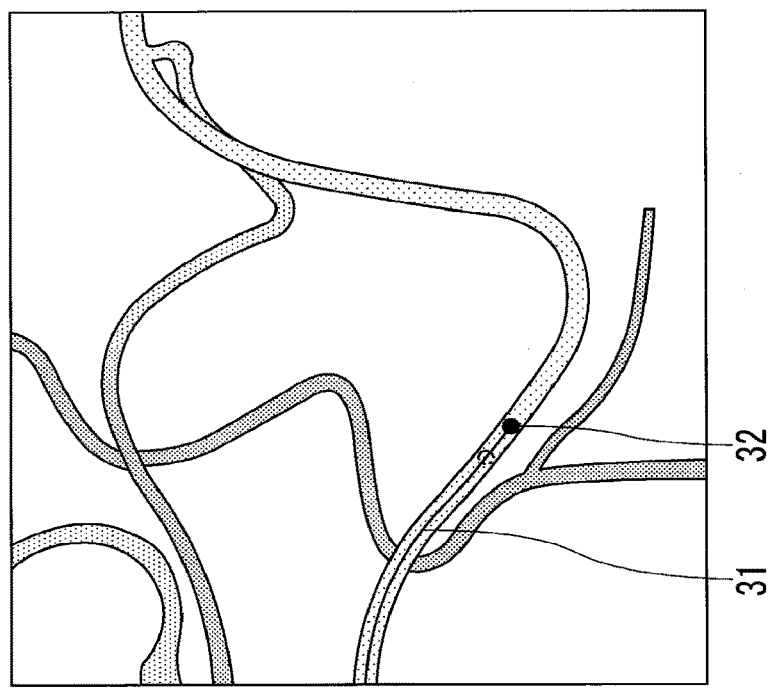
FIG. 9 is a diagram illustrating an example of a composite image using a PI road map image generated by a second PI road map image combining process shown in FIG. 8.
Figure 9:
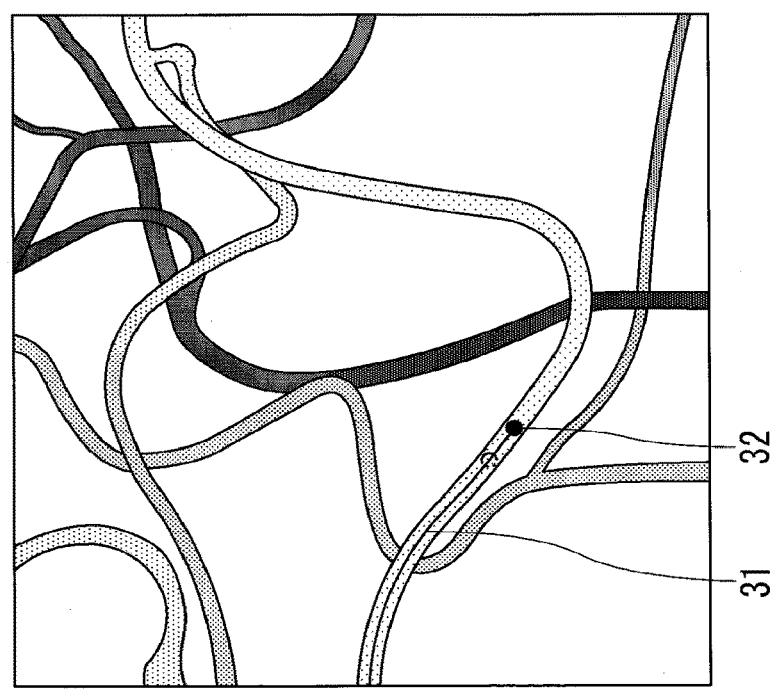

FIG. 9 is a diagram illustrating an example of a composite image using a PI road map image generated by a second PI road map image combining process shown in FIG. 8.

The second PI road map image combining process shown in FIG. 8 is a process of adopting, as the PI road map image, a partial image corresponding to the pixels having the parameter values in a predetermined range (e.g., V(Pn)−α≤V≤V(Pn)+α, V(Pn)−α≤V, V(Pn)+α, etc.) including the parameter value V(Pn) at the current position Pn of the portion of interest (distal end) 32 of the device (catheter) in the parameter image.

In step S21, the processing circuitry 25 uses the position locating function of the PI road map image combining function to identify the position in the parameter image of the distal end 32 of the catheter 31 inserted to a site of the object O.

Next, in step S22, the processing circuitry 25 uses the extraction function of the PI road map image combining function to extract pixels having parameter values in the predetermined range including the parameter value V(Pn) at the current position Pn of the distal end 32 of the catheter 31 (see the right part of FIG. 9).

Next, in step S23, the processing circuitry 25 uses the composite image generating function of the PI road map image combining function to generate, as the PI road map image, the partial image corresponding to the pixels extracted by the extraction function in the parameter image, and combines this image with the fluoroscopic image of the object O obtained in real time to generate the composite image.

The above procedures can adopt, as the PI road map image, the partial image that is in the parameter image and corresponds to the pixels having the parameter values in the predetermined range including the parameter value V(Pn) at the current position Pn of the distal end 32 of the catheter 31. As shown in FIG. 9, in the vascular image shown in the PI road map image generated by the second PI road map image combining process, blood vessels except those having parameter values at and around the parameter value of the current position Pn of the distal end 32 of the catheter 31 are not shown. Consequently, the PI road map image generated by the second PI road map image combining process also allows the user to easily discriminate between branching of the identical blood vessel and the intersection of blood vessels.

Figure 10:
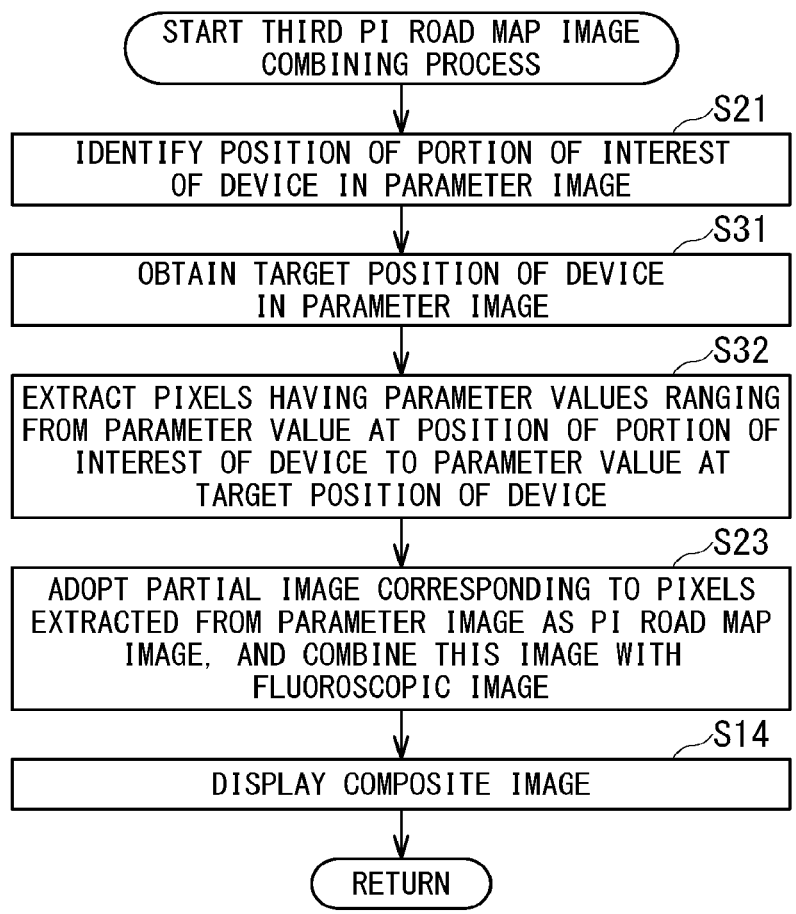
FIG. 10 is a subroutine flowchart showing an example of a third procedure of a PI road map image combining process executed by the PI road map image combining function in step S4 of FIG. 3.

FIG. 10 is a subroutine flowchart showing an example of a third procedure of a PI road map image combining process executed by the PI road map image combining function in step S4 of FIG. 3. Steps equivalent to those in FIGS. 5 and 6 are assigned the same symbols, and redundant description is omitted.

Figure 11:
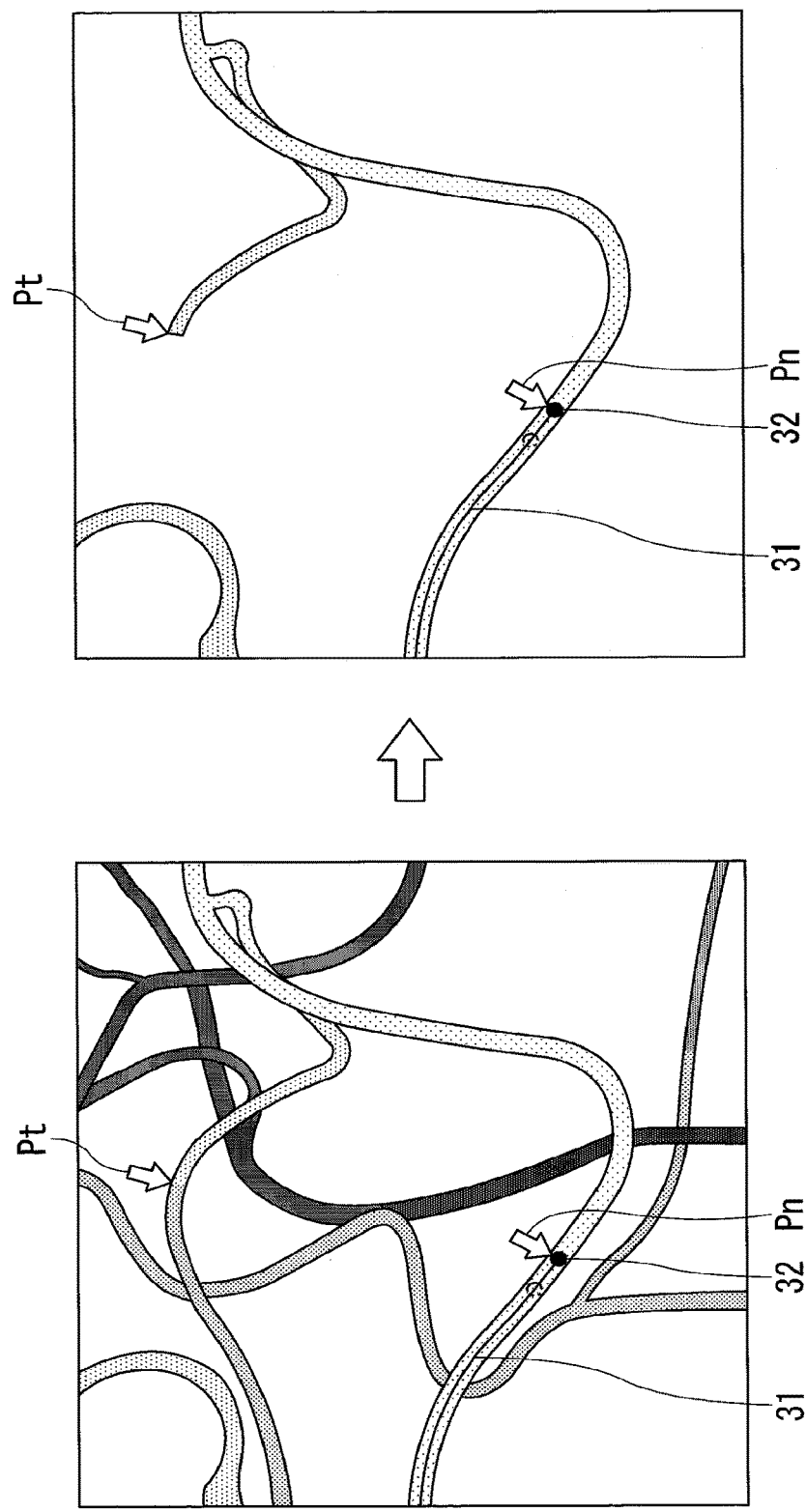
FIG. 11 is a diagram illustrating an example of a composite image using a PI road map image generated by a third PI road map image combining process shown in FIG. 10.

FIG. 11 is a diagram illustrating an example of a composite image using a PI road map image generated by a third PI road map image combining process shown in FIG. 10.

The third PI road map image combining process shown in FIG. 10 is a process of adopting, as the PI road map image, a partial image that is in the parameter image and corresponds to the pixels having the parameter values ranging from the parameter value V(Pn) at the current position Pn of the portion of interest of the device to the parameter value V(Pt) of the target position Pt of the device.

In step S31, the processing circuitry 25 uses the position locating function of the PI road map image combining function to identify the position in the parameter image of the target position Pt of the catheter 31 inserted to a site of the object O.

Next, in step S32, the processing circuitry 25 uses the extraction function of the PI road map image combining function to extract pixels having parameter values ranging from the parameter value V(Pn) at the current position Pn of the distal end 32 of the catheter 31 to the parameter value V(Pt) at the target position Pt of the device (see the right part of FIG. 11).

The above procedures can adopt, as the PI road map image, the partial image of the parameter image corresponding to the pixels having parameter values ranging from the parameter value V(Pn) at the current position Pn of the distal end 32 of the catheter 31 to the parameter value V(Pt) at the target position Pt of the device. As shown in FIG. 11, in the vascular image shown in the PI road map image generated by the third PI road map image combining process, blood vessels except those in a parameter value range from the value at the current position Pn of the distal end 32 of the catheter 31 to the value at the target position Pt are not shown. Consequently, the PI road map image generated by the third PI road map image combining process also allows the user to easily discriminate between branching of the identical blood vessel and the intersection of blood vessels.

As shown in FIGS. 8 and 10, in the case of setting the range of the parameter values and extracting pixels, many blood vessels other than those in the range of interest of blood vessels of interest are sometimes extracted. Thus, in the case of setting the range of the parameter values and extracting pixels, it is preferred that the extraction function further have a function that sequentially scan pixels from the pixel corresponding to the position of the portion of interest of the device in the direction approaching the parameter value at the target position of the device along the blood vessel, and extract only the pixels of the upper limit and lower limit of the range of parameter values or pixels scanned until reaching the target position of the device.

Figure 12:
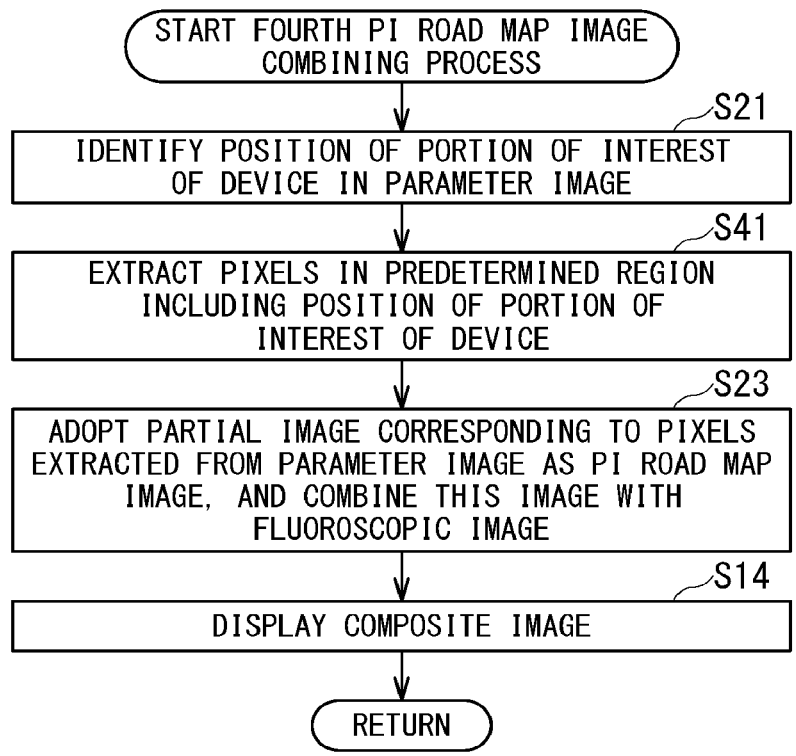
FIG. 12 is a subroutine flowchart showing an example of a fourth procedure of a PI road map image combining process executed by the PI road map image combining function in step S4 of FIG. 3.

FIG. 12 is a subroutine flowchart showing an example of a fourth procedure of a PI road map image combining process executed by the PI road map image combining function in step S4 of FIG. 3. Steps equivalent to those in FIGS. 5 and 6 are assigned the same symbols, and redundant description is omitted.

Figure 13:
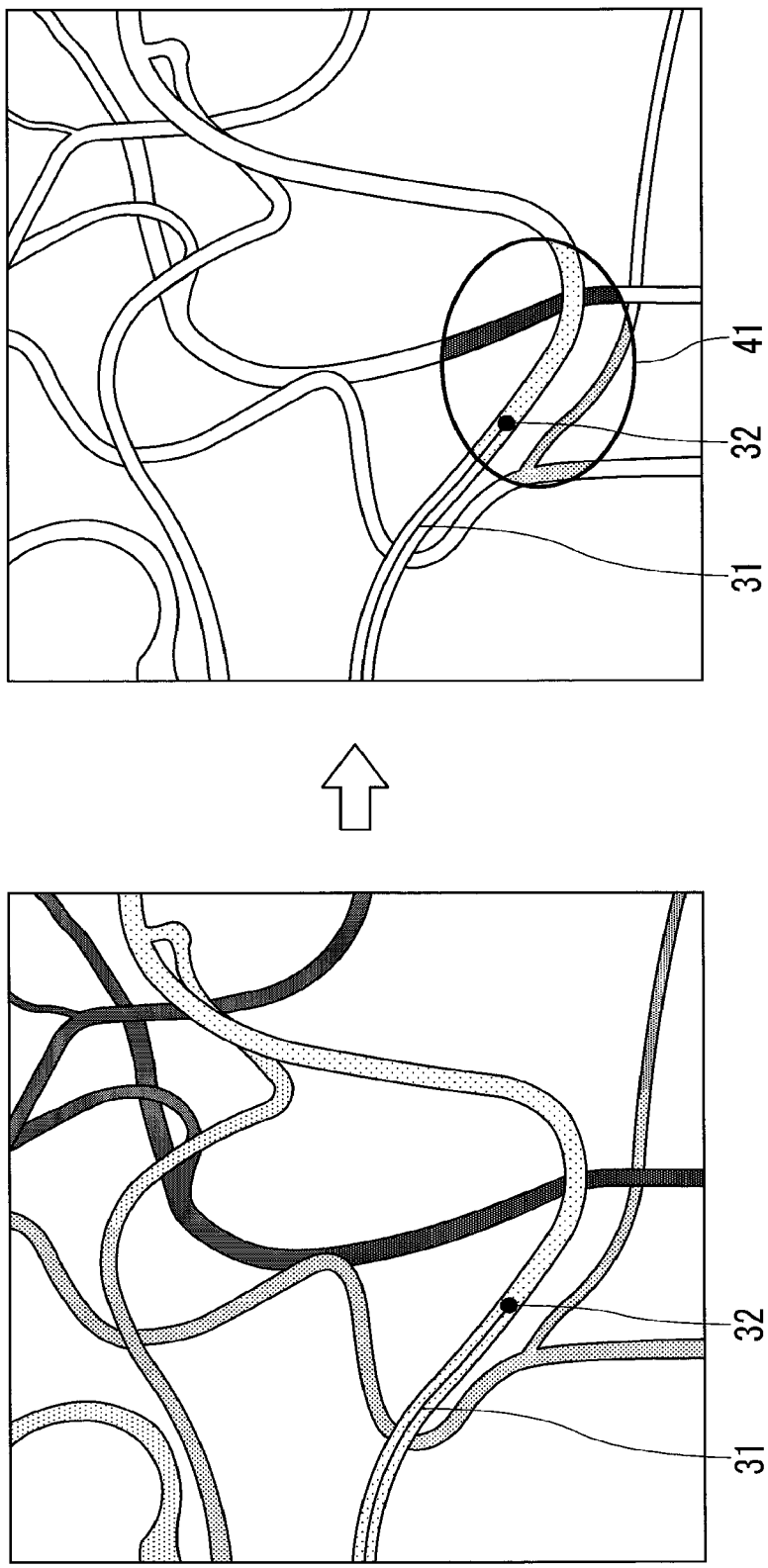
FIG. 13 is a diagram illustrating an example of a composite image using a PI road map image generated by a fourth PI road map image combining process shown in FIG. 12.

FIG. 13 is a diagram illustrating an example of a composite image using a PI road map image generated by a fourth PI road map image combining process shown in FIG. 12.

The fourth PI road map image combining process shown in FIG. 12 is a process of adopting, as the PI road map image, a partial image corresponding to pixels in a predetermined region 41 including the position of the portion of interest of the device. The predetermined region 41 may be any range that includes the position of the portion of interest of the device. The shape and range of this region is not limited to the example shown in FIG. 12.

In step S41, the processing circuitry 25 uses the extraction function of the PI road map image combining function to extract pixels in the predetermined region 41 including the current position Pn of the distal end 32 of the catheter 31 (see the right part of FIG. 13). Furthermore, the extraction function may extract the pixels in a predetermined region including the target position of the device at the same time.

The above procedures can adopt, as the PI road map image, the partial image that is in the parameter image and corresponds to the pixels in the predetermined region 41 including the current position Pn of the distal end 32 of the catheter 31. In the vascular image shown in the PI road map image generated by the fourth PI road map image combining process, blood vessels outside of the predetermined region 41 including the current position Pn of the distal end 32 of the catheter 31 are not shown. Consequently, the PI road map image generated by the third PI road map image combining process also allows the user to easily discriminate between branching of the identical blood vessel and the intersection of blood vessels.

The composite image generating function may generate the composite image with the setting where the transmittances of pixels of the blood vessel to which the portion of interest of the device belongs are lower than the transmittances of pixels of the other blood vessels. Alternatively, in the second to fourth PI road map image combining processes, the composite image generating function may further combine the portion of the parameter image other than the partial image adopted as the PI road map image in the parameter image with the composite image in a display mode different from that for the partial image. In this case, for example, the partial image that is in the parameter image and adopted as the PI road map image may be displayed in normal colors, while the portions of the parameter image other than the partial image may be color-displayed with transmittances set higher than those of the partial image.

Alternatively, in the second to fourth PI road map image combining processes, the composite image generating function may further combine the conventional fluoroscopic road map image with that in the region other than the partial image adopted as the PI road map image in the region of the composite image. As an example, the right part of FIG. 13 shows the composite image where the partial image adopted as the PI road map image is treated as a color image, and the conventional fluoroscopic road map image is combined in the region other than the partial image as a monochrome image. In this type of composite image (see the right part of FIG. 13), the color-displayed portion is small. Consequently, this image tends to be positively accepted by users familiar with the conventional monochrome fluoroscopic road map image. In the fluoroscopic road map image, a contrast still image showing a state where blood vessels are uniformly contrast-imaged or a white blank image of this image may be adopted as the road map image. Alternatively, moving images of contrast XA images or moving images consecutively showing multiple DSA images may be adopted.

The second to fourth PI road map image combining processes may always combine, as a part of the PI road map image, for example, an image of a blood vessel portion where the distal end 32 of the catheter 31 has passed, in order to make the locus of the distal end 32 of the catheter 31 easily discriminable.

Figure 14:
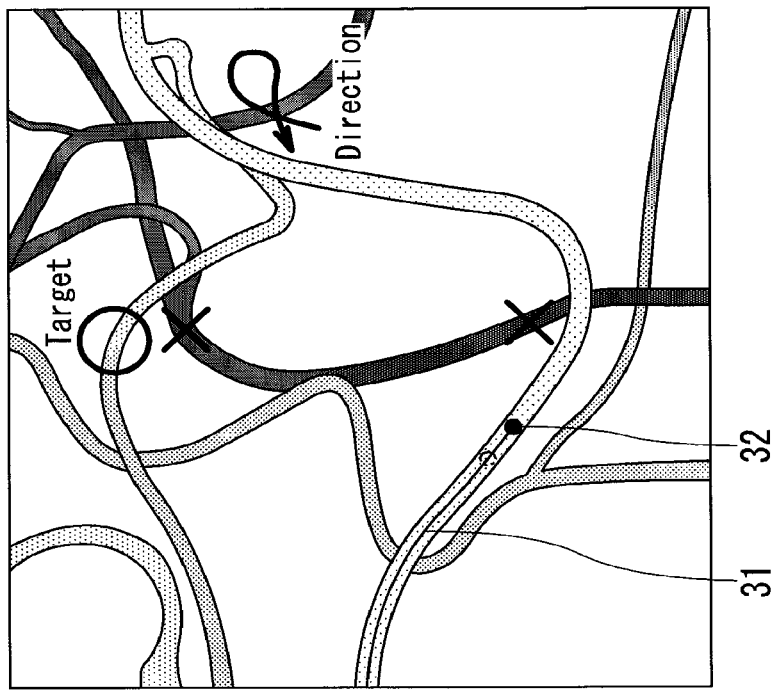
FIG. 14 is a diagram illustrating an example in the case of overlaying an annotation on the composite image.
Figure 14:
Figure 14:
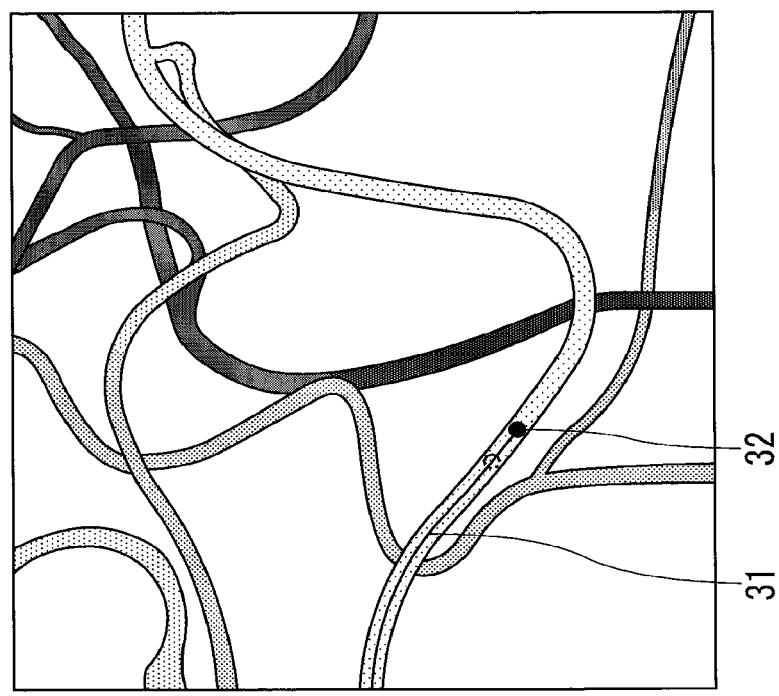

FIG. 14 is a diagram illustrating an example in the case of overlaying an annotation on the composite image. In FIG. 14, symbols, such as "Target", "Direction", "X" and an arrow, are examples of annotations added to the image.

As shown in FIG. 14, in the case where annotations are assigned to some or all of DSA images, the composite image, the X-ray fluoroscopic image or the parameter image, the PI road map image combining function may overlay the annotations on the composite image, and display this image on the display 21. In this case, the user can add the annotations through the input circuit 22 during a catheter procedure, thereby allowing these annotations to be easily overlaid on the PI road map image. Consequently, the user can more correctly operate the catheter while recognizing the annotations.

Subsequently, the parameter image generating process to be performed before the PI road map image combining process is briefly described.

Figure 15:
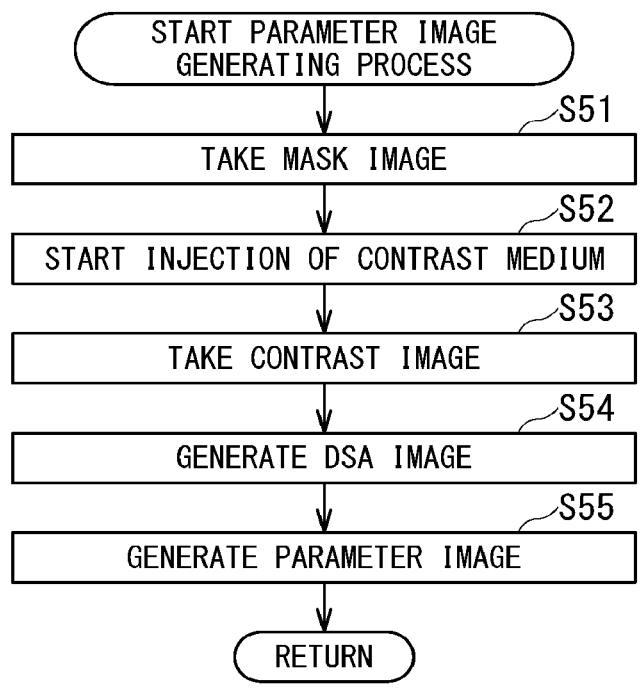
FIG. 15 is a flowchart showing an example of a parameter image generating process using the parameter value representing temporal information on blood flow.

FIG. 15 is a flowchart showing an example of a parameter image generating process using the parameter value representing temporal information on blood flow.

First, in step S51, the processing circuitry 25 uses the DSA image generating function to control the imaging executing function, and obtains image data (mask image data) before contrast medium administration, and causes the memory circuitry 23 to store the data.

Next, in step S52, the processing circuitry 25 uses the DSA image generating function to cause the injector 16 to start injection of the contrast medium into the object O.

Next, in step S53, the processing circuitry 25 uses the DSA image generating function to take temporally consecutive images when a predetermined time elapsed after start of contrast medium injection, under the same X-ray irradiation condition as that for mask image taking, and cause the memory circuitry 23 to store the obtained image data items (contrast image data items). Subsequently, the DSA image generating function causes the injector 16 to stop injection of the contrast medium into the object.

Next, in step S54, the processing circuitry 25 uses the DSA image generating function to read the mask image data and multiple contrast image data items from the image memory, and subtract the mask image data from each of the contrast image data items, thereby generating temporally consecutive multiple DSA image items of the object O (see FIG. 4).

Next, in step S55, the processing circuitry 25 uses the parameter image generating function to obtain the parameter values (e.g., TTA, TTP, etc.) representing temporal information on blood flow on the pixel-by-pixel basis, based on the time-intensity curve on each pixel in temporally consecutive DSA images of the object O and determine the pixel value of each pixel according to the parameter values representing the temporal information on blood flow to thereby generate the parameter image using the parameter values representing the temporal information on blood flow.

The above procedures can generate the parameter image using the parameter value representing temporal information on blood flow. The case of generating the parameter image using the DSA image has herein been described. Alternatively, the parameter image may be generated only from the images after contrast medium injection. In the case of generating the parameter image only from the images after contrast medium injection, the mask image data is not required.

Alternatively, the DSA image and the parameter image may be sequentially generated in real time and updated and displayed, while the contrast images are taken in real time. However, in the case of sequentially generating the DSA image and the parameter image in real time and using TTP as the parameter, the time phase of the peak cannot be determined without completion of fluoroscopy, in the strict sense. This is because there is a case where the peak intensity is reached in the last time phase. On the other hand, in a post-process that is a process after completion of taking the X-ray images in all the time phases after administration of the contrast medium, the value of TTP can be determined without any problem. In the case of sequentially generating the DSA image and the parameter image in real time while performing fluoroscopy in real time, TPP may be determined on the basis of, for example, the time phase of the peak in the range to the present time on the contrast medium time-intensity curve.

Alternatively, TTA based on a predetermined threshold may be adopted as the parameter, and the fluoroscopic images in real time may be colored in real time, thereby generating the PI road map image. Thus, according to the contrast medium administration, the blood vessels in the fluoroscopic image is sequentially colored, thereby allowing an operator to refer to the degree of branching of the blood vessels in an instant.

In the case of generating the PI road map image in real time, the parameter image is not necessarily generated. The real-time fluoroscopic images may be sequentially colored using the RGB values based on the parameter value, such as TTA.

The X-ray diagnostic apparatus 10 including the image processing apparatus 12 according to this embodiment can generate the PI road map image on the basis of the parameter image using the parameter value representing temporal information on blood flow, and combine this image with the fluoroscopic image of the object O obtained in real time to generate the composite image. The vascular image shown in the PI road map image has pixel values according to the parameter values representing temporal information on blood flow. Consequently, the X-ray diagnostic apparatus 10 including the image processing apparatus 12 according to this embodiment allows the user to easily discriminate between branching of the identical blood vessel and the intersection of blood vessels.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Further, although an example of processing the steps of the flowchart is described in the embodiments in which each steps are time-sequentially performed in order along the flowchart, each step of the flowchart may not be necessarily processed in a time series, and may be executed in parallel or individually executed.

For example, the parameter image using TTA and the parameter image using TTP may be preliminarily created by the parameter image generating function. In this case, the PI road map image combining function may switch the PI road map image to be combined with the fluoroscopic image between the parameter image using TTA and the parameter image using TTP according to an instruction by the user through the input circuit 22 or at predetermined timing.

The PI road map image combining function may switch the image to be combined with the fluoroscopic image between the PI road map image and the conventional fluoroscopic road map image according to an instruction by the user through the input circuit 22 or at predetermined timing.

Furthermore, in the case of extracting the pixels by the image extracting function, the PI road map image combining function may combine the partial image corresponding to the pixels extracted by the image extracting function in the conventional monochrome fluoroscopic road map image, instead of the partial image of the PI road map image, with the fluoroscopic image of the object O obtained in real time. This type of composite image tends to be positively accepted by users familiar with the conventional monochrome fluoroscopic road map image. The fluoroscopic road map image to be used at this time may be, for example, a contrast still image showing a state where blood vessels are uniformly contrast-imaged, or a white blank image of this image.

The parameter image generating function may generate any of a color image and a grayscale image using a typical color map, a grayscale map, a look-up table, and the like as a parameter image, respectively. Alternatively, a parameter image in a display mode other than the modes of these images may be generated. For example, the parameter image generating function may generate what is called CCC (Circular Color Coding) moving image as the parameter image. In the case of generating the CCC moving image, thresholds are set for the pixels on the basis of the peak time of bloodstream (e.g., 50% of the peak value is set as the threshold), and the elapsed time after the threshold is exceeded is adopted as the parameter value. The parameter values are assigned colors, thus determining the color of each pixel. The pixel value of each pixel is determined on the basis of a color bar having continuously changing colors, thereby allowing the color of each pixel to be sequentially changed and displayed. Thus, moving image representation can be achieved.

When movement of the C-arm 15, the bed 17, the tabletop 18 or the like is detected, the PI road map image combining function may automatically make the PI road map image invisible in the currently displayed composite image. This is because the imaging condition for the DSA image in order to generate the parameter image corresponding to the PI road map image is obviously different from that of the fluoroscopic image currently generated in real time. However, even when movement of the C-arm 15, the bed 17, the tabletop 18 or the like is detected but the C-arm 15, the bed 17, the tabletop 18 or the like is translated without any change in angle and without any rotational movement of the imaging visual field, the PT road map image may be translated so as to follow this translation.

The radiography apparatus 11 may have any configuration only with the X-ray detector 13 and the X-ray source 14 to allow an X-ray fluoroscopic imaging of the object O. Thus, the C-arm 15 is not an indispensable configuration element.

Further, the processing circuitry 25 in the above-described embodiments is an example of the processing circuitry described in the claims.

In addition, the term "processor" used in the explanation for controller 19 and processing circuitry 25 in the above-described embodiments, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit 23 and executing the programs.

Further, programs may be directly installed in the circuit of a processor instead of storing programs in the memory circuit 23. In this case, the processor implements various types of functions by reading out programs stored in its own circuit and executing the programs. Moreover, though a case where the unified processing circuitry 25 achieves each function has been explained above using FIG. 1, this is only an example. As another example, the processing circuitry 25 may be configured by combining a plurality of mutually independent processors so that each function is achieved by each processer that executes the corresponding program. When plural processors are provided for the processing circuitry, a memory circuit for storing the programs may be provided for each processor or one memory circuit 23 may collectively store all the programs corresponding to all the processors.

The invention claimed is:
1. An image processing apparatus, comprising:
processing circuitry configured to
calculate a parameter value for each pixel based on a change in time of a pixel value of the corresponding pixel in multiple image data items;
generate a parameter image such that each pixel of the parameter image has a pixel value according to the calculated parameter value of the corresponding pixel;
generate a composite image of an X-ray fluoroscopic image of an object obtained in real time and a road map image using at least a part of the parameter image; and
cause a display to display the composite image,
wherein the processing circuitry is further configured to:
identify a position in the parameter image of a portion of interest of a device inserted to a site of the object;
extract, from the parameter image, pixels having parameter values in a predetermined range including the parameter value at the position of the portion of interest of the device; and
generate, as the road map image, a partial image corresponding to the extracted pixels in the parameter image, generate the composite image of the X-ray fluoroscopic image of the object obtained in real time and the road map image, and cause the display to display the composite image.

2. The image processing apparatus according to claim 1, wherein the processing circuitry is further configured to:
calculate the parameter values on the pixel-by-pixel basis, based on a time-intensity curve on each pixel in temporally consecutive DSA images of the object, and generate the parameter image by determining the pixel value of each pixel according to the calculated parameter values; and
in a case where an annotation is assigned to some or all of the DSA images, the composite image, the X-ray fluoroscopic image or the parameter image, overlay the annotation on the composite image, and cause the display to display this image.

3. The image processing apparatus according to claim 1, wherein the processing circuitry is further configured to:
calculate the parameter values on the pixel-by-pixel basis, based on a time-intensity curve on each pixel in temporally consecutive DSA images of the object, and generate the parameter image by determining the pixel value of each pixel according to the calculated parameter values; and
in a case where an annotation is assigned to some or all of the DSA images, the composite image, the X-ray fluoroscopic image or the parameter image, overlay the annotation on the composite image, and cause the display to display this image.

4. The image processing apparatus according to claim 1, wherein the processing circuitry is further configured to generate the parameter image as a color image by determining the pixel value of each pixel based on a color map according to the calculated parameter value.

5. An image processing apparatus, comprising:
processing circuitry configured to
calculate a parameter value for each pixel based on a change in time of a pixel value of the corresponding pixel in multiple image data items;
generate a parameter image such that each pixel of the parameter image has a pixel value according to the calculated parameter value of the corresponding pixel;
generate a composite image of an X-ray fluoroscopic image of an object obtained in real time and a road map image using at least a part of the parameter image; and
cause a display to display the composite image,
wherein the processing circuitry is further configured to:
identify a position in the parameter image of a portion of interest of a device inserted to a site of the object and obtaining information on a target position of the device in the parameter image;
extract, from the parameter image, pixels having parameter values ranging from the parameter value of the position of the portion of interest of the device to the parameter value at the target position of the device; and
generate, as the road map image, a partial image corresponding to the extracted pixels in the parameter image, generate the composite image of the X-ray fluoroscopic image of the object obtained in real time and the road map image, and cause the display to display the composite image.

6. The image processing apparatus according to claim 1, wherein the processing circuitry is further configured to generate the road map image with a setting where transmittances of pixels of the blood vessel to which the portion of interest of the device belongs are lower than transmittances of pixels of other blood vessels.

7. The image processing apparatus according to claim 1, wherein the processing circuitry is further configured to:
calculate the parameter values on the pixel-by-pixel basis, based on a time-intensity curve on each pixel in temporally consecutive DSA images of the object, and generate the parameter image by determining the pixel value of each pixel according to the calculated parameter values; and
further combine the composite image with a moving image that sequentially shows the predetermined multiple DSA images at the site of the object, or with a contrast still image that shows a state where a blood vessel at the site of the object is uniformly contrast-imaged, the contrast still image being generated from the multiple DSA images.

8. The image processing apparatus according to claim 5, wherein the processing circuitry is further configured to generate the parameter image as a color image by determining the pixel value of each pixel based on a color map according to the calculated parameter value.

9. The image processing apparatus according to claim 5, wherein the processing circuitry is further configured to sequentially scan pixels from the pixel corresponding to the position of the portion of interest of the device in a direction approaching the parameter value at the target position of the device, and extract the pixels scanned until reaching the target position of the device.

10. The image processing apparatus according to claim 5, wherein the processing circuitry is further configured to generate the road map image with a setting where transmittances of pixels of the blood vessel to which the portion of interest of the device belongs are lower than transmittances of pixels of other blood vessels.

11. The image processing apparatus according to claim 5, wherein the processing circuitry is further configured to:
calculate the parameter values on the pixel-by-pixel basis, based on a time-intensity curve on each pixel in temporally consecutive DSA images of the object, and generate the parameter image by determining the pixel value of each pixel according to the calculated parameter values; and
further combine the composite image with a moving image that sequentially shows the predetermined multiple DSA images at the site of the object, or with a contrast still image that shows a state where a blood vessel at the site of the object is uniformly contrast-imaged, the contrast still image being generated from the multiple DSA images.

12. An image processing apparatus, comprising:
processing circuitry configured to
calculate a parameter value for each pixel based on a change in time of a pixel value of the corresponding pixel in multiple image data items;
generate a parameter image such that each pixel of the parameter image has a pixel value according to the calculated parameter value of the corresponding pixel;
generate a composite image of an X-ray fluoroscopic image of an object obtained in real time and a road map image using at least a part of the parameter image; and
cause a display to display the composite image,
wherein the processing circuitry is further configured to:
identify a position in the parameter image of a portion of interest of a device inserted to a site of the object;

extract, from the parameter image, pixels in a predetermined region including the position of the portion of interest of the device; and generate, as the road map image, a partial image corresponding to the extracted pixels in the parameter image, generate the composite image of the X-ray fluoroscopic image of the object obtained in real time and the road map image, and cause the display to display the composite image.

13. The image processing apparatus according to claim 12, wherein the processing circuitry is further configured to extract, from the parameter image, pixels in a predetermined region including a target position of the device.

14. An image processing apparatus comprising:
processing circuitry configured to
calculate a parameter value based on a change in time of a pixel value for each pixel of multiple image data items;
generate a parameter image by determining a pixel value of each pixel according to the calculated parameter value;
generate a composite image of an X-ray fluoroscopic image of an object obtained in real time and a road map image using at least a part of the parameter image; and
cause a display to display the composite image,
wherein the processing circuitry is further configured to:
generate as the parameter value, a first parameter image using a time in which a contrast medium reaches each pixel, and a second parameter image using a maximum intensity arrival time, based on a time-intensity curve for each pixel of the multiple image data items; and
switch the road map image to be combined with the X-ray fluoroscopic image of the object between the road map image based on the first parameter image and the road map image based on the second parameter image, according to an instruction by a user through an input device or at predetermined timing.

15. An image processing apparatus, comprising:
processing circuitry configured to
calculate a parameter value based on a change in time of a pixel value for each pixel of multiple image data items;
generate a parameter image by determining a pixel value of each pixel according to the calculated parameter value;
generate a composite image of an X-ray fluoroscopic image of an object obtained in real time and a road map image using at least a part of the parameter image; and
cause a display to display the composite image,
wherein the processing circuitry is further configured to
identify a position in the parameter image of a portion of interest of a device inserted to a site of the object;
extract, from the parameter image, pixels having parameter values in a predetermined range including the parameter value at the position of the portion of interest of the device;
generate, as the road map image, a partial image corresponding to the extracted pixels in the parameter image, generate the composite image of the X-ray fluoroscopic image of the object obtained in real time and the road map image, and cause the display to display the composite image,
generate, as the parameter value, a first parameter image using a time in which a contrast medium reaches each pixel, and a second parameter image using a maximum intensity arrival time, based on a time-intensity curve for each pixel of the multiple image data items; and
switch the road map image to be combined with the X-ray fluoroscopic image of the object between the road map image based on the first parameter image and the road map image based on the second parameter image, according to an instruction by a user through an input device or at predetermined timing.

16. An image processing apparatus, comprising:
processing circuitry configured to
calculate a parameter value based on a change in time of a pixel value for each pixel of multiple image data items;
generate a parameter image by determining a pixel value of each pixel according to the calculated parameter value;
generate a composite image of an X-ray fluoroscopic image of an object obtained in real time and a road map image using at least a part of the parameter image; and
cause a display to display the composite image,
wherein the processing circuitry is further configured to switch the road map image to be combined with the X-ray fluoroscopic image of the object between the road map image generated using at least a part of the parameter image, and a contrast still image that is generated from the multiple image data items and show a state where a blood vessel at the site of the object is uniformly contrast-imaged, according to an instruction by a user through an input device or at predetermined timing.

17. An image processing apparatus, comprising:
processing circuitry configured to
calculate a parameter value based on a change in time of a pixel value for each pixel of multiple image data items;
generate a parameter image by determining a pixel value of each pixel according to the calculated parameter value;
generate a composite image of an X-ray fluoroscopic image of an object obtained in real time and a road map image using at least a part of the parameter image; and
cause a display to display the composite image,
wherein the processing circuitry is further configured to
identify a position in the parameter image of a portion of interest of a device inserted to a site of the object;
extract, from the parameter image, pixels having parameter values in a predetermined range including the parameter value at the position of the portion of interest of the device;
generate, as the road map image, a partial image corresponding to the extracted pixels in the parameter image, generate the composite image of the X-ray fluoroscopic image of the object obtained in real time and the road map image, and cause the display to display the composite image, and
switch the road map image to be combined with the X-ray fluoroscopic image of the object between the road map image generated using at least a part of the parameter image, and a contrast still image that is generated from the multiple image data items and show a state where a blood vessel at the site of the object is uniformly contrast-imaged, according to an instruction by a user through an input device or at predetermined timing.

* * * * *